US009901290B2

(12) United States Patent
Najafi et al.

(10) Patent No.: US 9,901,290 B2
(45) Date of Patent: Feb. 27, 2018

(54) FALL DETECTION AND FALL RISK DETECTION SYSTEMS AND METHODS

(71) Applicant: BIOSENSICS LLC, Cambridge, MA (US)

(72) Inventors: Bijan Najafi, Highland Park, IL (US); Ashkan Vaziri, Brookline, MA (US); Ali-Reza Boloori, Ann Arbor, MI (US)

(73) Assignee: BIOSENSICS LLC, Watertown, MA (US)

( * ) Notice: Subject to any disclaimer, the term of this patent is extended or adjusted under 35 U.S.C. 154(b) by 273 days.

(21) Appl. No.: 14/659,446

(22) Filed: Mar. 16, 2015

(65) Prior Publication Data
US 2016/0100776 A1  Apr. 14, 2016

Related U.S. Application Data

(63) Continuation of application No. 13/531,313, filed on Jun. 22, 2012, now Pat. No. 9,005,141, which is a (Continued)

(51) Int. Cl.
*A61B 5/103* (2006.01)
*A61B 5/117* (2016.01)
(Continued)

(52) U.S. Cl.
CPC .......... *A61B 5/1117* (2013.01); *A61B 5/0004* (2013.01); *A61B 5/0022* (2013.01);
(Continued)

(58) Field of Classification Search
CPC .... A61B 5/1116; A61B 5/1117; A61B 5/1118; A61B 5/6823; A61B 5/746; A61B 2503/08; G08B 21/0446; G08B 21/043
See application file for complete search history.

(56) References Cited

U.S. PATENT DOCUMENTS 3,702,999 A    11/1972    Gradisar
5,373,651 A    12/1994    Wood
(Continued)

FOREIGN PATENT DOCUMENTS

EP        1195139 A1      4/2002
WO        WO 03/065891 A2    8/2003

OTHER PUBLICATIONS

Favre, J., et al., "Quaternion-based fusion of gyroscopes and accelerometers to improve 3D angle measurement", Electronic Letters, May 25, 2006, vol. 42, No. 11, 2 pages.
(Continued)

*Primary Examiner* — Devin Henson
(74) *Attorney, Agent, or Firm* — Knobbe, Martens, Olson & Bear LLP

(57) ABSTRACT

The present invention relates to a light-weight, small and portable ambulatory sensor for measuring and monitoring a person's physical activity. Based on these measurements and computations, the invented system quantifies the subject's physical activity, quantifies the subject's gait, determines his or her risk of falling, and automatically detects falls. The invention combines the features of portability, high autonomy, and real-time computational capacity. High autonomy is achieved by using only accelerometers, which have low power consumption rates as compared with gyroscope-based systems. Accelerometer measurements, however, contain significant amounts of noise, which must be removed before further analysis. The invention therefore uses novel time-frequency filters to denoise the measurements, and in conjunction with biomechanical models of human movement, perform the requisite computations, which may also be done in real time.

31 Claims, 10 Drawing Sheets

Related U.S. Application Data continuation of application No. 12/249,948, filed on Oct. 12, 2008, now Pat. No. 8,206,325.

(60) Provisional application No. 60/979,557, filed on Oct. 12, 2007.

(51) Int. Cl.
*A61B 5/11* (2006.01)
*A61B 5/00* (2006.01)
*G08B 21/04* (2006.01)

(52) U.S. Cl.
CPC ............. *A61B 5/112* (2013.01); *A61B 5/1116* (2013.01); *A61B 5/1118* (2013.01); *A61B 5/1123* (2013.01); *A61B 5/6823* (2013.01); *A61B 5/6831* (2013.01); *A61B 5/7203* (2013.01); *A61B 5/7225* (2013.01); *A61B 5/7264* (2013.01); *A61B 5/7275* (2013.01); *A61B 5/7282* (2013.01); *G08B 21/0446* (2013.01); *A61B 5/11* (2013.01); *A61B 5/746* (2013.01); *A61B 2503/08* (2013.01); *A61B 2505/07* (2013.01); *A61B 2505/09* (2013.01); *A61B 2562/0219* (2013.01); *G08B 21/043* (2013.01)

(56) References Cited

U.S. PATENT DOCUMENTS

| | | |
|---|---|---|
| 5,396,227 A | 3/1995 | Carroll et al. |
| 5,642,096 A | 6/1997 | Leyerer et al. |
| 5,697,791 A | 12/1997 | Nashner et al. |
| 5,907,819 A | 5/1999 | Johnson |
| 6,119,516 A | 9/2000 | Hock |
| 6,201,476 B1 | 3/2001 | Depeursinge et al. |
| 6,433,690 B2 | 8/2002 | Petelenz et al. |
| 6,730,024 B2 | 5/2004 | Freyre et al. |
| 6,890,285 B2 | 5/2005 | Rahman et al. |
| 6,895,341 B2 | 5/2005 | Barrey et al. |
| 6,926,667 B2 | 8/2005 | Khouri |
| 6,997,882 B1 | 2/2006 | Parker et al. |
| 7,141,026 B2 | 11/2006 | Aminian et al. |
| 7,166,063 B2 | 1/2007 | Rahman et al. |
| 7,334,472 B2 | 2/2008 | Seo et al. |
| 7,450,730 B2 | 11/2008 | Berg et al. |
| 7,620,450 B2 | 11/2009 | Kim et al. |
| 7,627,450 B2 | 12/2009 | Lee et al. |
| 7,632,216 B2 | 12/2009 | Rahman et al. |
| 7,634,379 B2 | 12/2009 | Noble |
| 7,640,134 B2 | 12/2009 | Park et al. |
| 7,701,354 B2 | 4/2010 | Chung |
| 7,725,289 B2 | 5/2010 | Nagashima et al. |
| 7,747,409 B2 | 6/2010 | Ladetto et al. |
| 7,771,371 B2 | 8/2010 | Avni |
| 7,857,771 B2 | 12/2010 | Alwan et al. |
| 7,890,291 B2 | 2/2011 | Godin et al. |
| 7,962,308 B2 | 6/2011 | Makino |
| 7,983,872 B2 | 7/2011 | Makino et al. |
| 8,007,450 B2 | 8/2011 | Williams |
| 8,025,632 B2 | 9/2011 | Einarsson |
| 8,109,890 B2 | 2/2012 | Kamiar et al. |
| 8,202,233 B2 | 6/2012 | Yasuhara |
| 8,206,325 B1 | 6/2012 | Najafi et al. |
| 8,212,650 B2 | 7/2012 | Tsern et al. |
| 8,242,879 B2 | 8/2012 | Haynes et al. |
| 8,287,477 B1 | 10/2012 | Herr et al. |
| 8,376,971 B1 | 2/2013 | Herr et al. |
| 8,384,551 B2 | 2/2013 | Ross et al. |
| 8,388,553 B2 | 3/2013 | James et al. |
| 8,551,029 B1 | 10/2013 | Herr et al. |
| 8,657,772 B2 | 2/2014 | Einarsson |
| 8,753,275 B2 | 6/2014 | Najafi et al. |
| 8,979,665 B1 | 3/2015 | Najafi et al. |
| 9,005,141 B1 | 4/2015 | Najafi et al. |
| 2001/0034014 A1 | 10/2001 | Nishimoto et al. |
| 2003/0065409 A1 | 4/2003 | Raeth et al. |
| 2003/0078528 A1 | 4/2003 | Rahman et al. |
| 2003/0139692 A1 | 7/2003 | Barrey et al. |
| 2004/0015103 A1 | 1/2004 | Aminian et al. |
| 2005/0043660 A1 | 2/2005 | Stark et al. |
| 2005/0165336 A1 | 7/2005 | Rahman et al. |
| 2006/0140425 A1 | 6/2006 | Berg et al. |
| 2006/0166157 A1 | 7/2006 | Rahman et al. |
| 2006/0270949 A1 | 11/2006 | Mathie et al. |
| 2007/0038268 A1 | 2/2007 | Weinberg et al. |
| 2007/0149359 A1 | 6/2007 | Rahman et al. |
| 2007/0270214 A1 | 11/2007 | Bentley |
| 2007/0293781 A1 | 12/2007 | Sims et al. |
| 2008/0091762 A1 | 4/2008 | Neuhauser et al. |
| 2008/0254822 A1 | 10/2008 | Tilley |
| 2008/0281555 A1 | 11/2008 | Godin et al. |
| 2008/0281636 A1 | 11/2008 | Jung et al. |
| 2008/0318683 A1 | 12/2008 | Rofougaran et al. |
| 2009/0002152 A1 | 1/2009 | Chung |
| 2009/0024065 A1 | 1/2009 | Einarsson |
| 2009/0048540 A1* | 2/2009 | Otto ...................... A61B 5/1118 600/595 |
| 2009/0055223 A1 | 2/2009 | Jung et al. |
| 2009/0058660 A1 | 3/2009 | Torch |
| 2009/0062696 A1 | 3/2009 | Nathan et al. |
| 2009/0069724 A1 | 3/2009 | Otto et al. |
| 2009/0076345 A1 | 3/2009 | Manicka et al. |
| 2009/0099495 A1 | 4/2009 | Campos et al. |
| 2009/0192414 A1 | 7/2009 | Yasuhara |
| 2009/0195350 A1 | 8/2009 | Tsern et al. |
| 2009/0234249 A1 | 9/2009 | Randolph |
| 2009/0292194 A1 | 11/2009 | Libbus et al. |
| 2009/0293319 A1 | 12/2009 | Avni |
| 2010/0121227 A1 | 5/2010 | Stirling et al. |
| 2010/0174576 A1 | 7/2010 | Naylor |
| 2010/0211185 A1 | 8/2010 | van der Merwe et al. |
| 2010/0286571 A1 | 11/2010 | Allum et al. |
| 2010/0324455 A1 | 12/2010 | Rangel et al. |
| 2011/0054359 A1 | 3/2011 | Sazonov et al. |
| 2011/0115629 A1 | 5/2011 | Holler et al. |
| 2012/0022667 A1 | 1/2012 | Accinni et al. |
| 2013/0245785 A1 | 9/2013 | Accini et al. |

OTHER PUBLICATIONS

Najafi, B., et al., "An Ambulatory System for Measuring and Monitoring Physical Activity and Risk of Falling and for Automatic Fall Detection", U.S. Appl. No. 60/979,557, filed Oct. 12, 2007.

U.S. Appl. No. 13/723,040, Najafi et al.

U.S. Appl. No. 14/616,522, Najafi et al.

American Diabetes Association, Apr. 7-8, 1999, Boston, Massachusetts, "Consensus development conference in diabetic foot wound care", Diabetes Care 22.8:1354 (Aug. 1999).

Aminian et al., "Spatio-temporal parameters of gait measured by an ambulatory system using miniature gyroscopes," *Journal of Biomechanics*, vol. 35:689-699 (2002).

Aminian et al., "Temporal feature estimation during walking using miniature accelerometers: an analysis of gait improvement after hip arthroplasty," *Medical & Biological Engineering & Computing*, vol. 37:686-691 (1999).

Armstrong et al., "Activity patterns of patients with diabetic foot ulceration", Diabetes Care, vol. 26(9):2595-2597 (2003).

Armstrong et al., "Continuous activity monitoring in persons a high risk for diabetes-related lower-extremity amputation", Journal of the American Podiatric Medical Association, vol. 91:451-455 (2001).

Armstrong et al., "Evaluation of removable and irremovable cast walkers in the healing of diabetic foot wounds: a randomized controlled trial", Diabetes Care, vol. 28:551-4 (2005).

Armstrong et al., "Variability in activity may precede diabetic foot ulceration", Diabetes Care, vol. 27(8):3028-3029 (2004).

Bohannon et al., "Walking speed: reference values and correlates for older adults," *J Orthop Sports Phys Ther*, vol. 24:86-90 (1996).

Brand, Paul W. "The diabetic foot", Diabetes Mellitus, Theory and Practice, 3rd Ed., Ellenberg M. Rifkin H., Ed. New York: Medical Examination Publishing, 1983, pp. 803-828.

(56) References Cited

OTHER PUBLICATIONS

Coleman et al., "The total contact cast, a therapy for plantar ulceration on insensitive feet", J.Am. Podiatr. Med. Assoc., vol. 74:548-552 (1984).
Cummings et al., "Forgetting falls. The limited accuracy of recall of falls in the elderly," *J Am Geriatr Soc*, vol. 36:613-6 (1988).
Doughty et al., "The design of a practical and reliable fall detector for community and institutional telecare," *J Telemed Telecare*, vol. 6 Suppl 1:S150-4 (2000).
Helm et al., "Total contact casting in diabetic patients with neuropathic foot ulcerations", Arch. Phys. Med. Rehabil., vol. 65:691-693 (1984).
Lavery et al., "Reducing dynamic foot pressures in high-risk diabetic subjects with foot ulcerations", Diabetes Care, vol. 19(8):818-821 (1996).
Lindemann et al., "Evaluation of a fall detector based on accelerometers: a pilot study," *Med Biol Eng Comput*, vol. 43:548-51 (2005).
Mathie et al., "Detection of daily physical activities using a triaxial accelerometer," Medical & Biological Engineering & Computing, 2003, vol. 41, pp. 296-301.
Mizell, "Using gravity to estimate accelerometer orientation", Proceedings of the Seventh IEEE International Symposium on Wearable Computers, Computer Society (2003).
Najafi et al., "A novel ambulatory device for continuous 24-H monitoring of physical activity in daily life", North American Congress on Biomechanics (NACOB), Michigan, 2008.
Najafi et al., "Ambulatory system for human motion analysis using a kinematic sensor: Monitoring of daily physical activity in the elderly," *Ieee Transactions on Biomedical Engineering*, vol. 50:711-723 (2003).
Najafi et al., "Assessing Postural Control and Postural Control Strategy in Diabetes Patients Using Innovative and Wearable Technology", Jour. Diab. Science and Tech. vol. 4(4):780-791 (2010).
Najafi et al., "Measurement of standsit and sit-stand transitions using a miniature gyroscope and its application in fall risk evaluation in the elderly," *Ieee Transactions on Biomedical Engineering*, vol. 49:843-851 (2002).
Noury et al., "A smart sensor based on rules and its evaluation in daily routines," presented at 25th Annual International Conference of the IEEE Eng. Med. Biol. Society (2003).
Oliver et al., "Development and evaluation of evidence based risk assessment tool (STRATIFY) to predict which elderly inpatients will fall: case-control and cohort studies," *Bmj*, vol. 315:1049-53 (1997).
Pecoraro et al., "Pathways to diabetic limb amputation", Diabetes Care, vol. 13(5):513-521 (1990).
Sinacore et al., "Diabetic plantar ulcers treated by total contact casting", Phys. Ther. vol. 67:1543-1547 (1987).
Tinetti et al., "Fall risk index for elderly patients based on number of chronic disabilities," *Am J Med*, vol. 80: 429-34 (1986).
Walker et al., "Chronic diabetic neuropathic foot ulcerations and total contact casting: healing effectiveness and outcome predictability", Arch. Phys. Med. Rehabil., vol. 66:574 (1985).
Wu et al., "The pivotal role of offloading in the management of neuropathic foot ulceration", Curr. Diab. Rep. vol. 5:423-9 (2005).
Wu et al., "Use of pressure offloading devices in diabetic foot ulcers", Diabetes Care, vol. 31(11):2118-2119, (2008).
Tiedemann, A. et al., "The comparative ability of eight functional mobility tests for predicting falls in community-dwelling older people" Age and Ageing 2008, May 16, 2008, 37:430-435.

\* cited by examiner

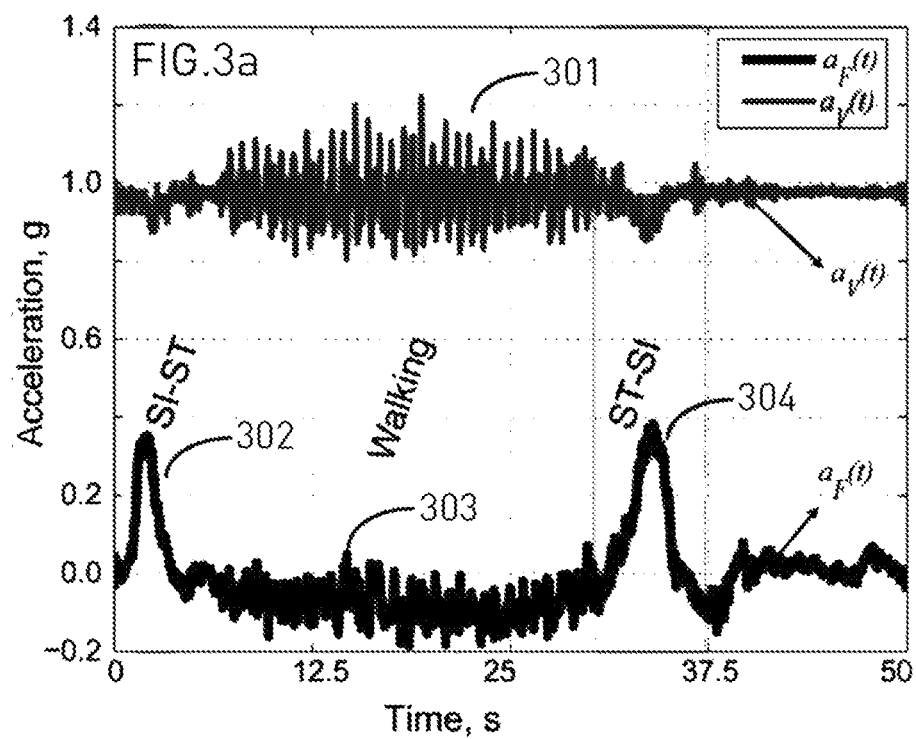
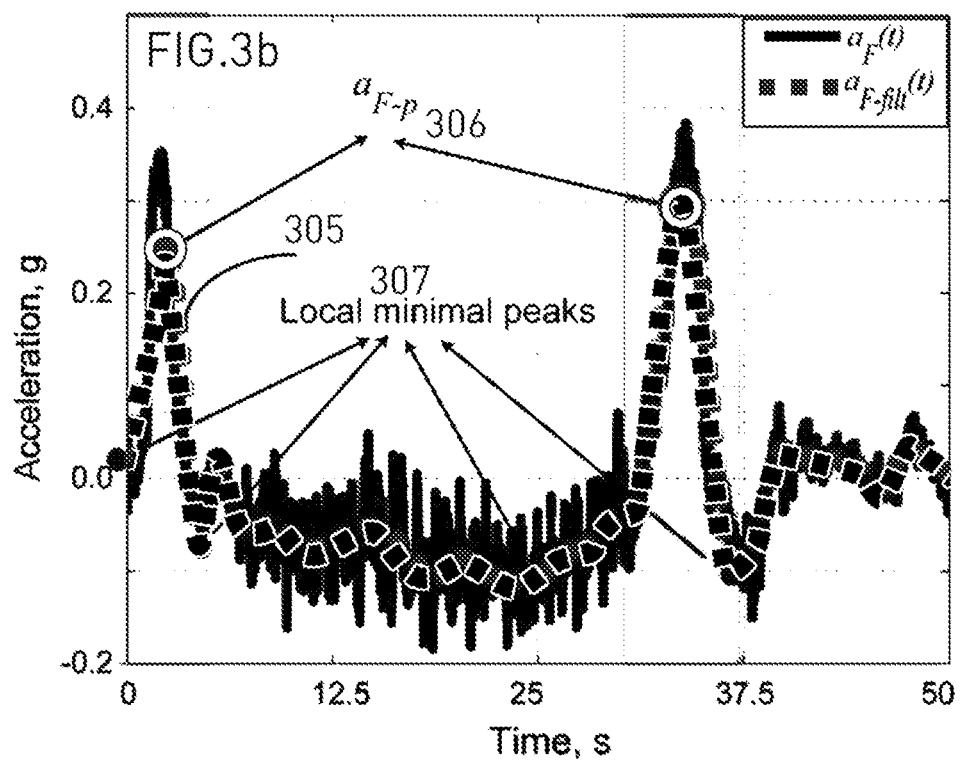

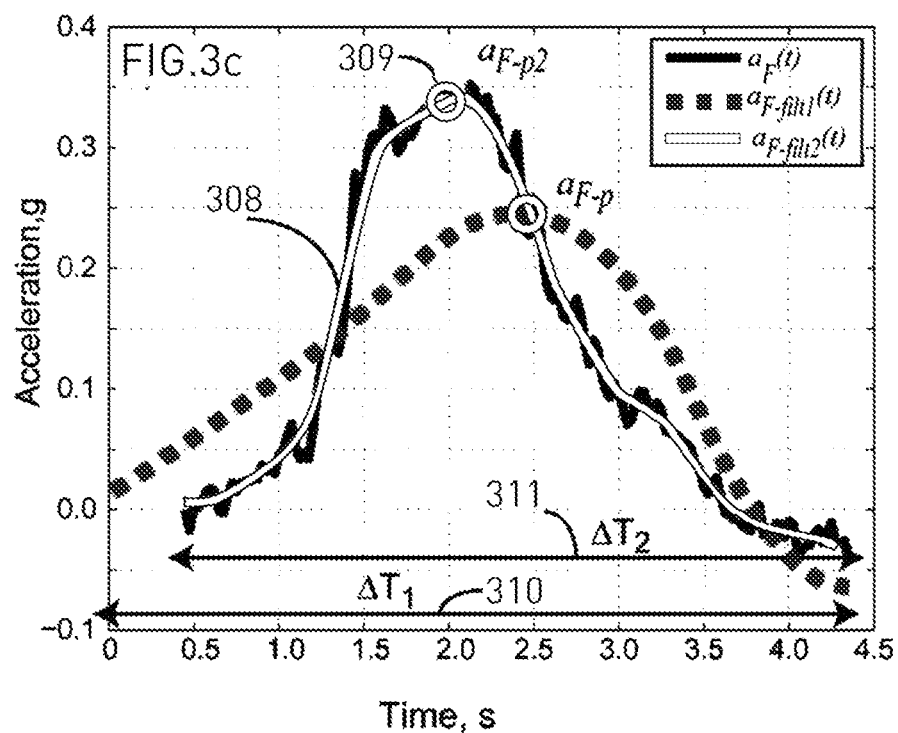
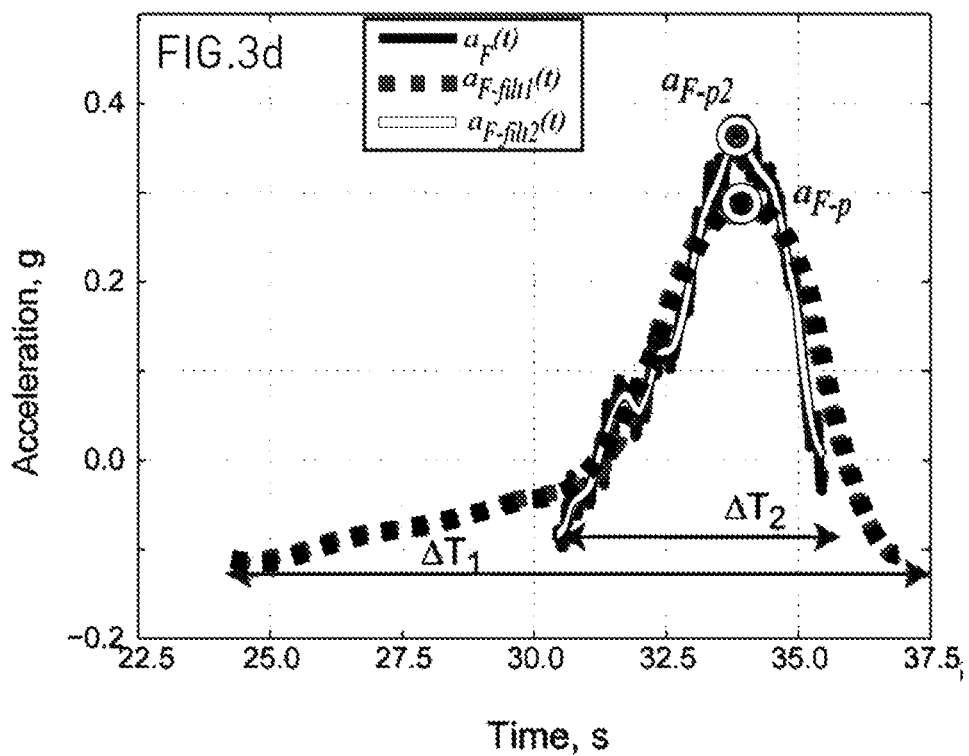

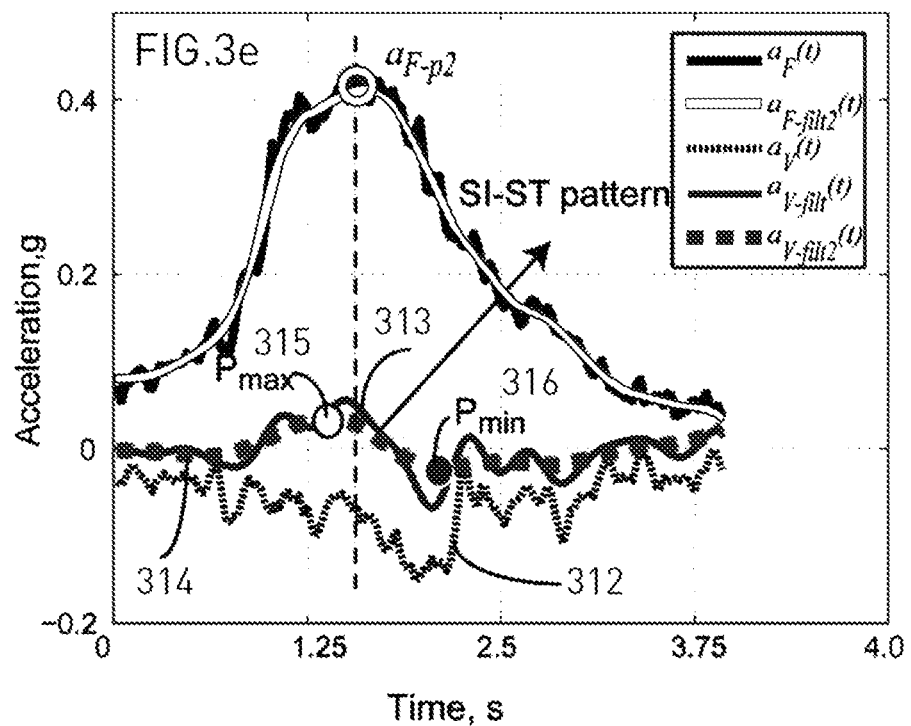
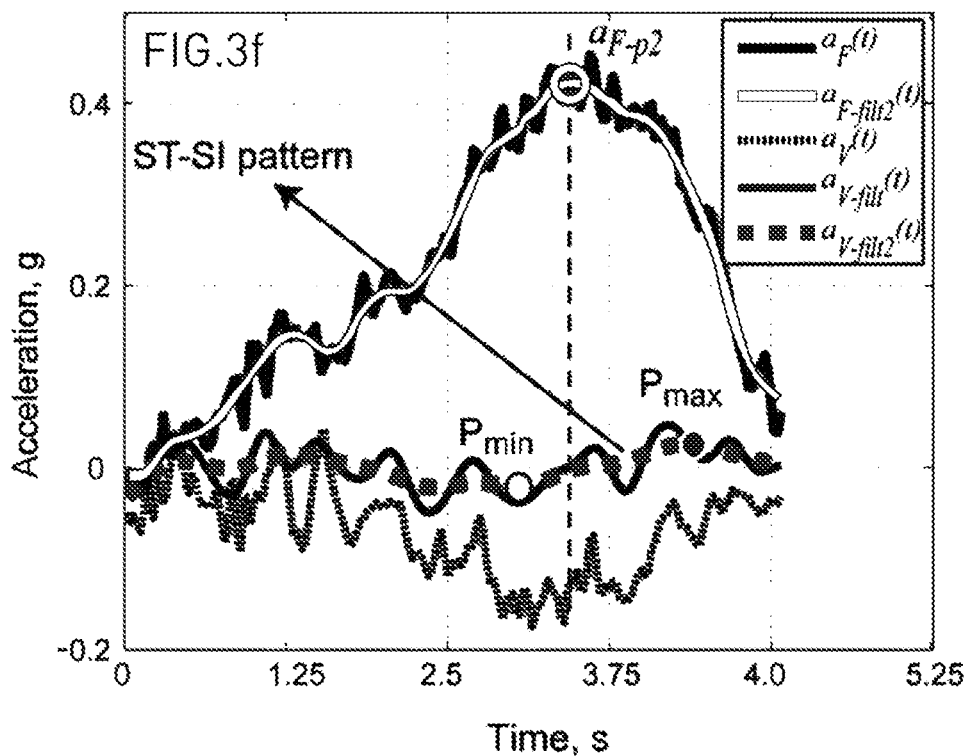

FALL DETECTION AND FALL RISK DETECTION SYSTEMS AND METHODS

CROSS-REFERENCE TO RELATED APPLICATIONS

This application is a continuation of U.S. patent application Ser. No. 13/531,313, filed Jun. 22, 2012 which is a continuation of U.S. patent application Ser. No. 12/249,948, filed Oct. 12, 2008, now U.S. Pat. No. 8,206,325, which claims the benefit of U.S. Provisional Application No. 60/979,557, filed Oct. 12, 2007, each of which is incorporated herein in its entirety by reference.

FIELD

This invention generally relates to body movement monitoring systems, specifically to an ambulatory system which (1) measures and quantifies parameters related to the user's postures and movements; (2) evaluates the user's risk of falling; and (3) automatically detects the user's falls.

BACKGROUND OF THE INVENTION

We envision several uses for the present invention. In the fields of elderly care and physical therapy, the present invention finds several important uses. We envision that the invented system can provide both qualitative and quantitative monitoring of an elderly person's physical activity (PA) during his or her everyday life. This information is useful for several reasons: first, PA monitoring can accurately determine the user's state of physical and mental health, identifying subacute changes in their health status. For example, this system can detect early deteriorations in the amount and quality of the subjects' PA due to various health conditions (e.g., congestive heart failure, development of infections, etc.) Second, PA monitoring provides valuable information about the sequence of the elderly person's movements during the time window surrounding their falls. This information significantly aids the development of alert systems to predict, and ideally, prevent fall occurrences. Third, assessment of the effects of new drugs and pain treatments are significantly advanced through monitoring of the subjects' physical activity during his or her everyday life. Fourth, monitoring of PA in the elderly population can, over time, provide insight into qualitative and quantitative changes in PA as a result of all adverse physical events, such as functional declines or hospitalizations. Persons at risk can therefore be identified, and novel preventive interventional methods may be tailored to their needs. The invented system also finds use in remote monitoring and telecare of people suffering from various diseases, such as Alzheimer's, as well as of those recovering and rehabilitating from diseases and medical procedures.

In clinical research and studies, the invented system provides valuable insight into the mechanisms and factors influencing physical activity and balance by quantifying the subject's PA and risk of falling (RoF) in all contexts, including everyday life.

In drug development, the invented system can be used to study the role of various drugs and treatment procedures on the physical activity and RoF of people during clinical studies.

In athletics training, this system provides valuable feedback on the user's body movements, and can be a valuable tool for both training and on-field performance measurement.

Measurement and monitoring of PA by the present invented system also finds use in weight management by providing intelligent feedback to the user about his or her daily energy expenditures.

Postural Transitions:

Najafi et al. [1-3] have developed algorithms for identifying postural transitions (PT), e.g., sit-to-stand (SI-ST) and stand-to-sit (ST-SI) from data recorded by a gyroscopic sensor attached to the subject's trunk. The high power-consumption rates of gyroscopes, however, severely limits the applicability of these algorithms for applications outside of the laboratory (which include everyday life applications), since such a system has an autonomy of only a few hours, therefore requiring frequent recharging or exchanges of the battery. Although the addition of more batteries would increase the device's autonomy, it will also increase its size and weight, thus hindering the subject's natural movements.

By contrast, the algorithms developed as part of the present invention use accelerometer data in place of gyroscope data, and therefore enable long-term, autonomous operability of the system.

Gait Analysis:

Proper gait function (i.e., quality of gait) requires the ability to maintain safe gait while navigating in complex and changing environments, and to conform one's gait to different task demands. Furthermore, a person's quality of gait is closely linked to his or her overall state of health. For example, walking speed correlates with the individual's ability to live independently, with the ability to perform various activities of daily life (such as safely crossing a traffic intersection), and with reductions in the risk of falling [4].

Since evaluation of a person's overall health and quality of life are greatly facilitated by knowledge of his or her gait function during everyday life, a system that can automatically extract gait-related parameters with minimal hindrance of the user's movements is highly useful. To date, however, fully satisfactory methods and systems have not been developed. Current techniques for computing a person's gait parameters are primarily based on the use of vertical accelerometer signals, together with a peak-detection algorithm to identify the walking step. Such techniques, however, possess several important shortcomings.

First, they cannot remove the rotational artifacts generated by the body segment to which the sensor has been attached. These noise artifacts stem from the gravitational component of the accelerometer signal. While they can be easily removed in the case of healthy young subjects, such artifacts pose a key challenge to accurate computation of gait parameters in the case of patients and the elderly—who tend to walk slowly and may use walking aids. Second, current algorithms cannot discriminate between acceleration peaks associated with postural transitions, and those due to walking steps, thus leading to very low specificity during activity daily life (ADL).

Alternative technologies for estimating the gait pattern use combinations of gyroscopes and/or accelerometers attached to the lower limbs [5-7]. Use of gyroscopes decreases the autonomy of the system due to high power consumption. Moreover, attaching the sensors on lower limbs hinders the user's movements, who must carry the system during ADL.

The present invention accurately identifies the user's walking periods during ADL, discriminates between left and right gait steps, and estimates the spatiotemporal parameters of gait (e.g., swing, stance, double support, and gait speed) using only accelerometers. Aminian et al. (1999) [7] have suggested an algorithm, based on a neural network, that extracts spatio-temporal parameters of gait using accelerometers attached to the subject's lower back. This algorithm, however, requires a calibration/pre-learning stage that can only be accomplished by having subjects walk within a constrained space of a gait lab. This requirement renders that algorithm impractical for use during everyday life activities. By contrast, the algorithms developed as part of the present invention require no initial calibrations, and therefore can be easily used by any individual.

In so doing, our algorithms overcome the shortcomings present in the prior art: the small, lightweight and portable sensory module, attached to the subject's chest, poses minimal hindrance to his or her movements during ADL. Furthermore, the accelerometers consume considerably less power than do gyroscopes, leading to significantly longer operational times. Moreover, the invented system provides significantly higher accuracy in discriminations, and better removes rotational noise artifacts.

Risk of Falling:

Evaluation of the individual's risk of falling is required in providing adapted assistance and preventive measures for subjects deemed at a high risk of falling. This risk is generally evaluated by using questionnaires, which have shortcomings such as subjectivity and limited accuracy in recall [8]. Risk of falling can also be evaluated by clinical and functional tests, such as assessments of posture and gait, independence in daily life, cognition, and vision [9-10]. However, an objective method for remotely monitoring this risk through the monitoring the daily physical activity (PA) has not yet been developed. By contrast, the present invention assesses and monitors the user's risk of falling through monitoring and measurement of his or her daily physical activity.

Automatic Fall Detection:

Of the health problems commonly associated with aging, the most serious is falling—defined as a person's trunk, knee, or hand unintentionally coming to rest on the ground or a lower level below the waist. A reliable system to remotely detect falls allows delivery of early care to these persons, and decreases the detrimental consequences of falls, leading to substantial health-care cost savings. Current fall alarm systems require activation and are therefore inappropriate in falls due to syncope, a loss of consciousness associated with cerebro-vascular accidents. Moreover, persons suffering from Alzheimer's disease—affecting approximately one-third of persons aged 80 years and older—may not be capable of activating such systems. A reliable system capable of sending automatic alarms when assistance is necessary will therefore provide an innovative way to support these patients and their caregivers. Automatic fall reporting would also be important in clinical research to reliably record occurrence of falls.

Current detection of falls essentially relies on self-reporting and complex reporting systems with daily phone-call reminders. In fact, for the research community interested in fall prevention, the documentation of falls is a methodological pitfall, and no unanimously accepted method for reporting falls exists. Little data support claims to the reliability and validity of different reporting systems. Oral reports have many limitations due to the cognitive status of the subjects as well as mental factors such as shame or fear of reporting. Finally, fall events associated with loss of consciousness due to syncope, stroke or epileptic seizures are not always recognized.

While a number of different approaches to fall detection have appeared in recent years [11-14], they have primarily used patterns recorded by tri-axial accelerometers to identify shocks related to falls, independent of the previous posture (i.e. sitting, lying, standing) and/or the state of activity (e.g. rest, walking, turning, postural transition, etc) of the faller. Not using the key information about the person's previous posture and state of activity likely gives rise to false detections, dramatically decreasing the accuracy of the fall detector. The present invention, by contrast, identifies falls with high sensitivity and specificity using only signals from accelerometers.

SUMMARY

The present invention consists of a body movement monitoring system that includes a sensing unit, attachable to the upper part of the user's body, such as trunk or shoulder, comprising a tri-axial accelerometer, or, three mono-axial accelerometers measuring accelerations in three perpendicular directions. The system also includes one or more processor circuits configured to: process the signals recorded by the accelerometer(s) and derive information related to the subject's movement from said accelerometer(s). Some or all of these analyses may be carried out on-board the sensing unit. In all cases, software-based algorithms, developed as part of the present invention, are integrated with the processor circuits performing the analyses. One or more data storage systems are also included in the system, and are configured to store signals recorded by said accelerometer(s), or the information derived by one of said processor circuits, or both. One or more of said data storage systems may be housed within said sensor. An optional communications system, configured to transmit at least a portion of the data recorded by said accelerometers, or at least a portion of the information derived by said the processor circuit housed within the sensor, or both, may also be housed with the sensor. The information derived from the measured acceleration signals are used to monitor and quantify the user's physical activity; automatically detect the user's risk of falling; and assess the user's risk of falling. The required computations are performed according to software-based algorithms, developed as part of the present invention, which use at least one biomechanical model of human body movement, and one or more signal processing time-frequency filters.

BRIEF DESCRIPTION OF THE DRAWINGS

The foregoing and other objects, features, and advantages of the invention will be apparent from the following detailed description of the invention, as illustrated in the accompanying drawings, in which like reference numerals designate like parts throughout the figures thereof and wherein:

FIGS. 3a-f demonstrate the operation of the algorithms in determining the time, type and duration of the subject's postural transitions;

DETAILED DESCRIPTION OF EXEMPLARY EMBODIMENTS

The present invention consists of a system and method for performing the following tasks during the user's everyday life: (1) monitoring the user's physical activity; (2) automatically detecting the user's falls; and (3) assessing the user's risk of falling. The second and third tasks are based on the results obtained from the first.

Figures 1A, 1B:
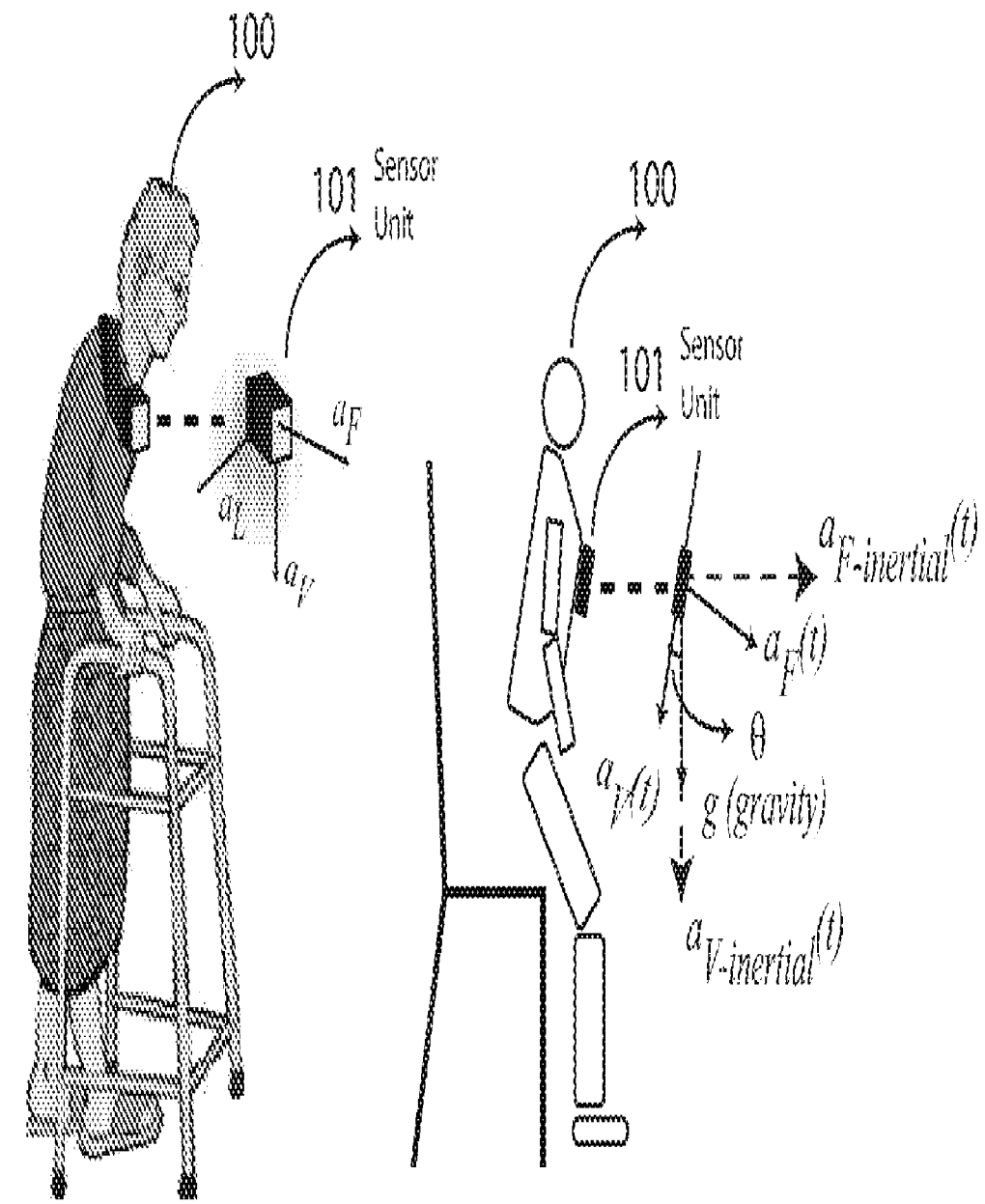
FIG. 1a illustrates how an elderly subject may wear the sensory module, and also shows the three components of acceleration measured by the sensory unit.
FIG. 1b is a two-dimensional schematic of a subject wearing the sensory unit, and shows the subject's trunk lean angle θ, the direction of gravity, as well as the frontal and vertical acceleration components.

As shown by FIG. 1a, the system includes a sensing module ("SM") 101 for sensing, filtering and analyzing the user's 100 body movements. The SM 101 is positioned on the user's 100 upper body (typically, on the user's chest or torso), and is comprised of one to three accelerometers, each of which may be mono-axial or multi-axial. The only constraints on the accelerometer configuration are that (1) accelerations in three perpendicular directions must be measured; and (2) the accelerometer(s) is(are) configured to record accelerations in the frontal (F), vertical (V) and lateral (L) directions, which directions are relative to the user 100 (see FIG. 1a). In this document, all acceleration quantities are expressed in units of g (i.e., as multiples or fractions of g), where g is the gravitational constant equaling 9.81 m/s$^2$: for example, by this convention an acceleration magnitude of 9.81 m/s$^2$ (in SI units) will be expressed 1.

The SM 101 may also include a data-storage system for storing the measured accelerations. An optional on-board communications system provides the SM 101 the capability to transmit the collected data and/or analyzed signals through either wired or wireless links for storage and/or for further offline analysis.

Analysis of the measured acceleration signals may be carried out (1) entirely on-board the SM 101, (2) partially on-board the SM 101 and partially at other location(s), or (3) entirely at other location(s). In case some or all of the analysis is (are) carried out on-board the SM 101, a data processing circuit will be included on-board the SM to carry out the required computations according to software-based algorithms developed as part of the present invention. In case some or all of the analysis is carried at location(s) separate from the SM 101, the required data processing circuits performing the analysis may be ordinary or special-purpose computers, and are integrated with software-based algorithms developed as part of the present invention.

A. Monitoring the User's Physical Activity

Monitoring the user's physical activity consists of monitoring and assessing the user's postures, movements, trunk tilt, as well as fall-related task parameters. To this end, the system computes various parameters associated with the subject's movement from the data recorded by the SM 101. These parameters consist of: (a) the subject's trunk tilt (specified in degree, measuring the angle between the subject's trunk axis, and the axis aligned with the gravitational force—see FIG. 1b); (b) the type of the subject's postural transitions (PT); (c) the time of the subject's postural transitions; (d) the duration of the subject's postural transitions; (e) the duration of the subject's locomotion; (f) characterization of the subject's locomotion (gait analysis); and (g) the type of subject's postures (e.g., sitting, standing, lying).

Use of accelerometers in place of gyroscopes by the present invention allows for long-term autonomous operability of the system. The associated challenges introduced by this replacement, however, consist of processing the resulting noisy accelerometer signals during everyday living activities.

I. Identifying the Types of Postural Transitions, and Computing their Durations and Occurrences:

The flowchart in FIG. 2 and FIGS. 3a-3f demonstrate the operation of the algorithms, developed as part of the present invention, used to continuously determine the type, time, and duration of the subject's postural transitions (in this case, SI-ST and ST-SI) during everyday movements. The algorithms use the frontal and vertical accelerometer signals—$a_F(t)$ and $a_V(t)$ respectively in FIG. 1a—where their time-varying nature is explicitly shown by including the time variable t in the notation used for these signals. In implementing the algorithms, the time variable t is by necessity discrete.

FIG. 3a shows an example of the acceleration patterns recorded by the vertical and frontal accelerometers from an elderly subject with a high risk of falling ($a_V(t)$: gray line 301; $a_F(t)$: black line). As identified on the plot, the pattern consists of a sit-to-stand (SI-ST) postural transition followed by a period of walking and turning, followed by another postural transition (stand-to-sit; ST-SI).

Figure 2:
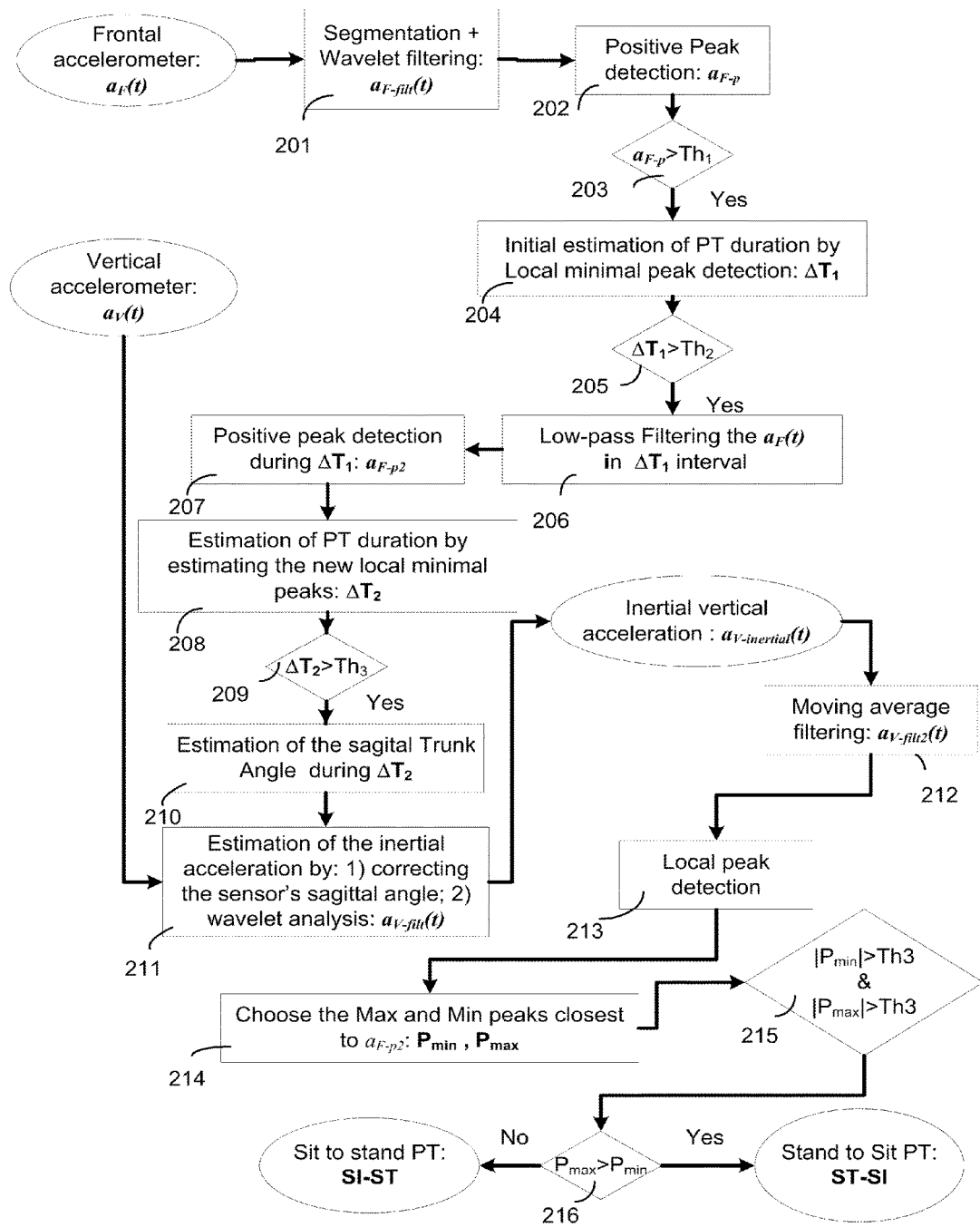
FIG. 2 is a flowchart of the algorithms used to determine the time, time and duration of the subject's postural transitions.

As shown in FIG. 2, the algorithm performs the following steps on the frontal accelerometer signal to determine the occurrence, duration and type of the postural transitions:

1) segmenting, followed by wavelet filtering (box 201 in FIG. 2) to remove signal artifacts induced by locomotion (e.g., walking, climbing or descending the stairs, etc.)—see also the white trace 305 in FIG. 3b, an example of the resulting filtered signal $a_{F-filt}(t)$;

2) locating the local maximum peaks (denoted by $a_{F-p}$ 306 in FIG. 3b) in the filtered signal $a_{F-filt}(t)$ 305 through a peak-detection algorithm—this step corresponds to box 202 in FIG. 2;

3) for each postural transition, corresponding to a particular $a_{F-p}$ 306, computing an initial estimate of the postural transition duration ($\Delta T_1$) by (boxes 203 and 204):
   (i) determining whether $a_{F-p}$ 306 is greater than a pre-defined threshold Th1;
   (ii) if yes, locating the local minima 307 in $a_{F-filt}(t)$ 305, within a specified time window, that precede and follow the particular maximum peak $a_{F-p}$ 306 see FIG. 3b;
   (iii) computing $\Delta T_1$ 310 as the duration of the resulting time interval $I_1$ separating the local minima computed above.

The above steps suppress and remove signal artifacts, such as noisy peaks, associated with shocks or other locomotion activities.

Following the initial determination of the postural transition duration ($\Delta T_1$), the system computes a more accurate estimate of the postural transition duration, $\Delta T_2$, by applying additional filters to the frontal acceleration signal only within a time interval that is centered at $I_1$, but that is typically 10% to 30% longer in duration than $\Delta T_1$ 310. Such filtering of the frontal acceleration signal significantly decreases the requisite calculation costs, therefore enabling real-time implementation of the algorithm.

If the value $\Delta T1$ 310 surpasses a defined threshold, $Th_2$ (box 205 in FIG. 2), the following steps are performed on the frontal accelerometer signal $a_F(t)$ only during a time interval that is centered at $I_1$ but that is typically 10% to 30% longer in duration:

1) as represented by box 206 in FIG. 2, low-pass filtering the aF(t) signal during the time interval $I_1$ by a wavelet;
2) as represented by box 207 in FIG. 2, locating the maximum peak ($a_{F-p2}$ 309) in the resulting filtered signal $a_{F-filt2}(t)$ 308 during time interval $I_1$ (see FIG. 3c);
3) within a specified time window, locating a local minimum in $a_{F-filt2}(t)$ closest to, and preceding, the particular maximum peak $a_{F-p2}$ (box 207 in FIG. 2);
4) within a specified time window, locating a local minimum in $a_{F-filt2}(t)$ closest to, and following the same maximum peak (box 207 in FIG. 2);
5) computing $\Delta T_2$ 311 (see FIG. 3c) as the duration of the resulting time interval $I_2$ separating the local minima computed above (box 207 in FIG. 2);

The time of the maximum peak $a_{F-p2}$ represents the time of the postural transition, and the parameter $\Delta T_2$ 311 represents the estimate of the duration of the postural transition.

For each postural transition, following the computation of its time of occurrence and its duration, the system uses the step-by-step algorithm below to identify its type (e.g., ST-SI or ST-SI):

1) as represented by boxes 209 and 210 in FIG. 2, for each postural transition if $\Delta T_2$ exceeds a predefined threshold $Th_3$, estimate the trunk tilt angle in the sagittal plane, $\theta$, using a low-pass filtering of the $a_F(t)$ signal during the corresponding time interval $I_2$—since $a_F(t)$ consists of a $\theta$-dependent gravitational component as well as a higher frequency, pure frontal-acceleration component, low-pass filtering removes the pure frontal-acceleration component, leading to a quantity proportional to the $\sin(\theta)$;
2) estimate the time-varying inertial frontal and vertical accelerations $a_{F-inertial}(t)$ and $a_{V-inertial}(t)$ through the following coordinate transformation (see box 211 in FIG. 2):

$$\begin{bmatrix} a_{F-inertial}(t) \\ a_{V-inertial}(t) \end{bmatrix} = \begin{bmatrix} \cos(\theta(t)) & -\sin(\theta(t)) \\ \sin(\theta(t)) & -\cos(\theta(t)) \end{bmatrix} \begin{bmatrix} a_F(t) \\ a_V(t) \end{bmatrix} + \begin{bmatrix} 0 \\ 1 \end{bmatrix},$$

where, as mentioned before, the acceleration signal is expressed in units of g (g represents the gravitational constant (9.81 m/s$^2$))—see also FIG. 1b for a free-body diagram showing the inertial acceleration components;

3) in parallel, apply an adequate, cascaded low-pass filter to remove the artifacts from $a_V(t)$, where the low-pass filter functions as follows:
   (i) removal of the gravitational component of $a_V(t)$ 312 (FIG. 3e) using the following equations (see also box 211 in FIG. 2):

$a_F(t)=[a_{V-inertial}(t)+1] \sin(\theta(t))+a_{F-inertial}(t)\cos(\theta(t));$ $a_V(t)=[a_{V-inertial}(t)+1] \cos(\theta(t))+a_{F-inertial}(t)\sin(\theta(t));$ $a_{V-filt}(t)=\sqrt{[a_F(t)]^2+[a_V(t)]^2};$ (ii) low-pass filtering the resulting signal $a_{V-filt}(t)$ 313, leading to $a_{V-filt}2$ (t); and (iii) filtering this signal by a moving-average filter to obtain $a_{V-filt}3$ (t) (see also box 212 in FIG. 2);
4) as exemplified in FIGS. 3e-3f, determine the local peaks in $a_{V-filt3}(t)$ using a peak detection algorithm (box 213 in FIG. 2); the resulting positive and negative peaks—$P_{max}$ 315 and $P_{min}$ 316, respectively—exceeding a predefined threshold $Th_4$, are identified (boxes 214 and 215 in FIG. 2);
5) classify the detected postural transition as sit-to-stand or stand-to-sit through the sequence by which $P_{max}$ and $P_{min}$ occur: e.g., a $P_{max}$ followed by a $P_{min}$ identifies the postural transition as a sit-to-stand pattern (box 316 in FIG. 2; see also FIGS. 3e-3f);
6) apply a post-processing algorithm to prevent misclassification of postures and postural transitions: for each postural transition, the classification as ST-SI or SI-ST will be corrected based on the preceding and subsequent sequences of postural transitions.

Figure 4:
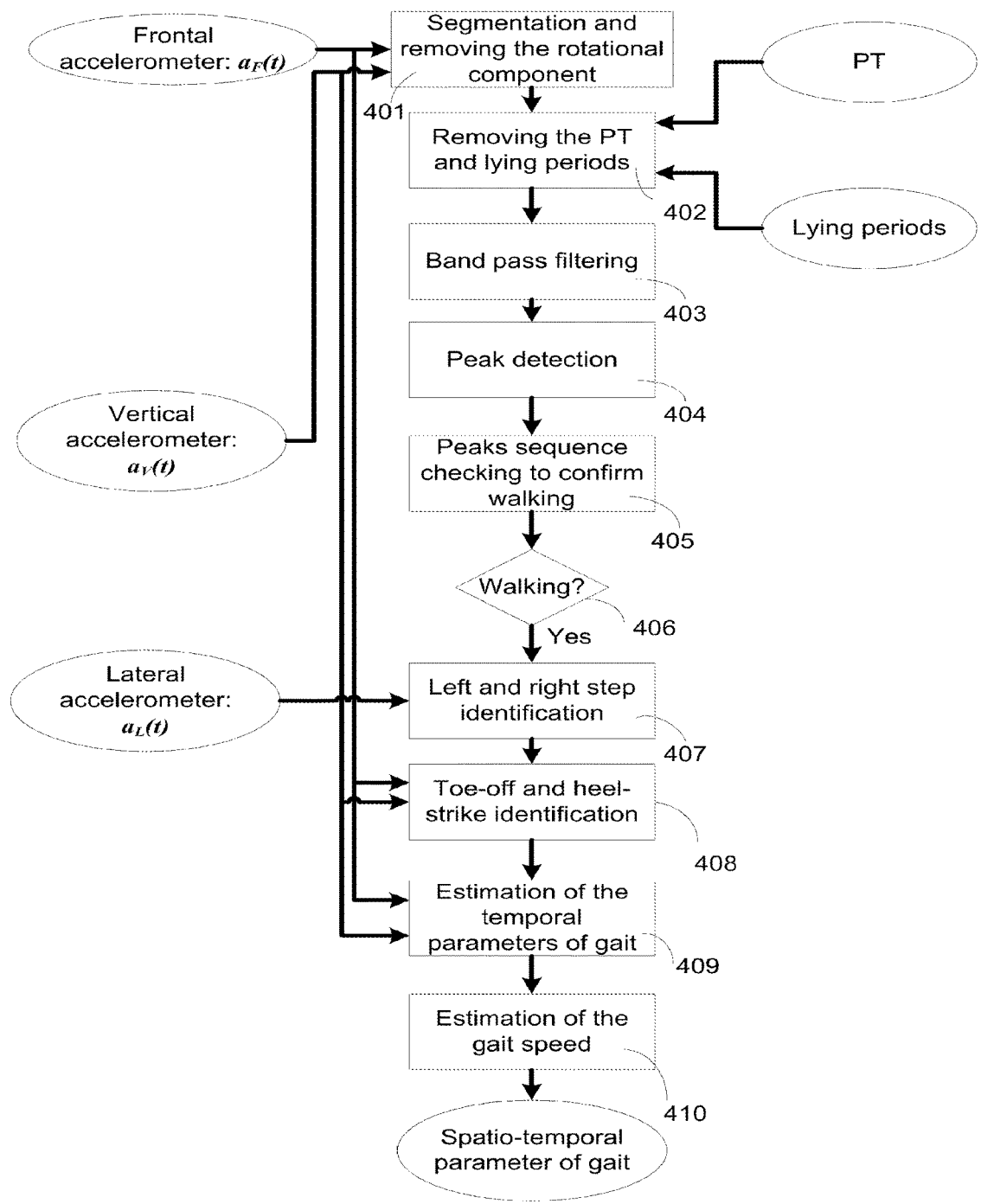
FIG. 4 is a flowchart of the algorithms used to identify the walking periods, and to compute the subject's spatiotemporal parameters of gait.

II. Analyzing Gait, and Identifying the Corresponding Walking Periods:

FIG. 4 describes in flowchart form the software-based algorithm, developed as part of the invented system, to identify the subject's walking periods and measure his or her gait parameters. Using data recorded by the accelerometers, the algorithm can distinguish left and right gait steps, as well estimate the spatiotemporal gait parameters, e.g., swing, stance, double support, and gait speed.

Figure 5:
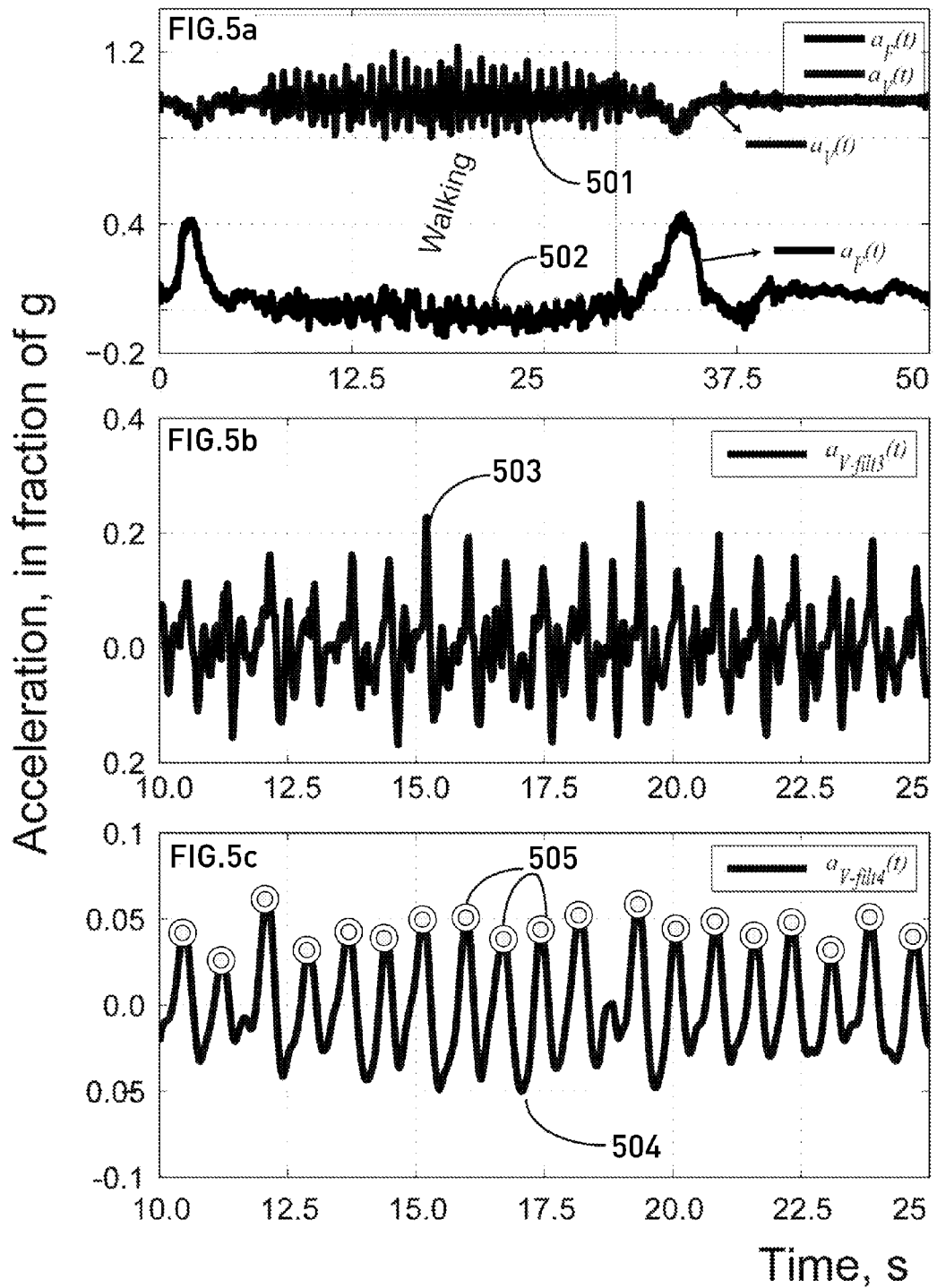
FIGS. 5a-c demonstrate the operation of the algorithms in identifying the walking periods, and in computing the subject's spatio-temporal parameters of gait.

The algorithm consists of the following steps:
1) remove from consideration data during time periods associated with postural transitions and lying (boxes 401-402 in FIG. 4);
2) compute the time-varying norm (i.e., time-varying magnitude) of the vertical and horizontal accelerometer signals as:

$a_F(t)=[a_{V-inertial}(t)+1] \sin(\theta(t))+a_{F-inertial}(t)\cos(\theta(t));$ $a_V(t)=[a_{V-inertial}(t)+1] \cos(\theta(t))+a_{F-inertial}(t)\sin(\theta(t));$ $a_{V-filt}(t)=\sqrt{[a_F(t)]^2+[a_V(t)]^2};$ where $\theta(t)$ represents the time-varying trunk angle, and $a_{V-inertial}(t)$ and $a_{F-inertial}(t)$ represent the time-varying vertical and frontal acceleration components, respectively; FIG. 5b shows the resulting waveform, $a_{V-filt3}(t)$ 503—see FIG. 1b for the free-body diagram leading to the above formulas; these formulas allow for suppression of the movement artifacts derived from the rotations of the subject's trunk;

3) remove the gravitational component from the vertical acceleration signal in two steps: first, use formula stated in step (2) to compute aV-filt3(t) 503; second, as shown by box 403 in FIG. 4, band-pass filter the result, leading to $a_{V-filt4}(t)$ 504 (see FIG. 5c);
4) as represented by box 404 in FIG. 4, identify gait steps as the peaks 505 (see, FIG. 5c) in the $a_{V-filt4}(t)$ signal 504;
5) verify the sequence of the detected peaks according to pre-defined conditions for gait patterns (box 405 in FIG. 4);
6) distinguish left and right steps (box 407 in FIG. 4) using the signal $a_L(t)$ from the lateral accelerometer—specifically, (i) the subject's lateral velocity $v_L(t)$ is computed by integrating $a_L(t)$ during the recognized walking periods; (ii) the relationship between the locations of the positive and negative peaks in $v_L(t)$ with the identified peak in the filtered vertical acceleration signal, $a_{V-filt4}(t)$ 504, allows for left and right steps be distinguished.

This algorithm, furthermore, enables both the recognition of undetected gait steps, and the removal of false detected steps.

The system, through another algorithm, computes the times of heel-strike (initial contact) and toe-off (final contact) events using information extracted from the frontal and vertical acceleration signals—this step corresponds to box 408 in FIG. 4. Specifically, the local minimum and maximum peaks in the frontal acceleration signal surrounding each identified vertical acceleration peak are used to identify heel-strike event and toe-off events. Following a heel-strike event, the subject's trunk continues to moves forward. As the toe-off event occurs, the trunk slows down, leading to a negative peak in the frontal accelerometer signal. Although a heel-strike event can be estimated using the vertical acceleration signal, when an impact is identified, the positive peak of the frontal acceleration pattern offers a significantly lesser noisy source for identification of the heel-strike event. Determination of these event times facilitates the measurement of the temporal parameters (e.g., stance, swing, double support, step time, gait cycle time, etc.) and other relevant information associated with the spatial parameters (i.e. stride velocity, step length and stride length).

Gait speed (i.e., stride velocity) is computed (box 410 in FIG. 4) using information from the detected gait cycle and the amplitude of acceleration during the double support.

III. Detecting and Classifying the Lying Posture.

The system distinguishes lying from sitting and standing by comparing the angle of the vertical accelerometer signal $a_V(t)$ to that of the gravitational component. While the vertical accelerometer measures almost zero during lying periods, its value is significantly greater during sitting and upright postures—in some cases the value is close to the gravitational constant.

Figure 6:
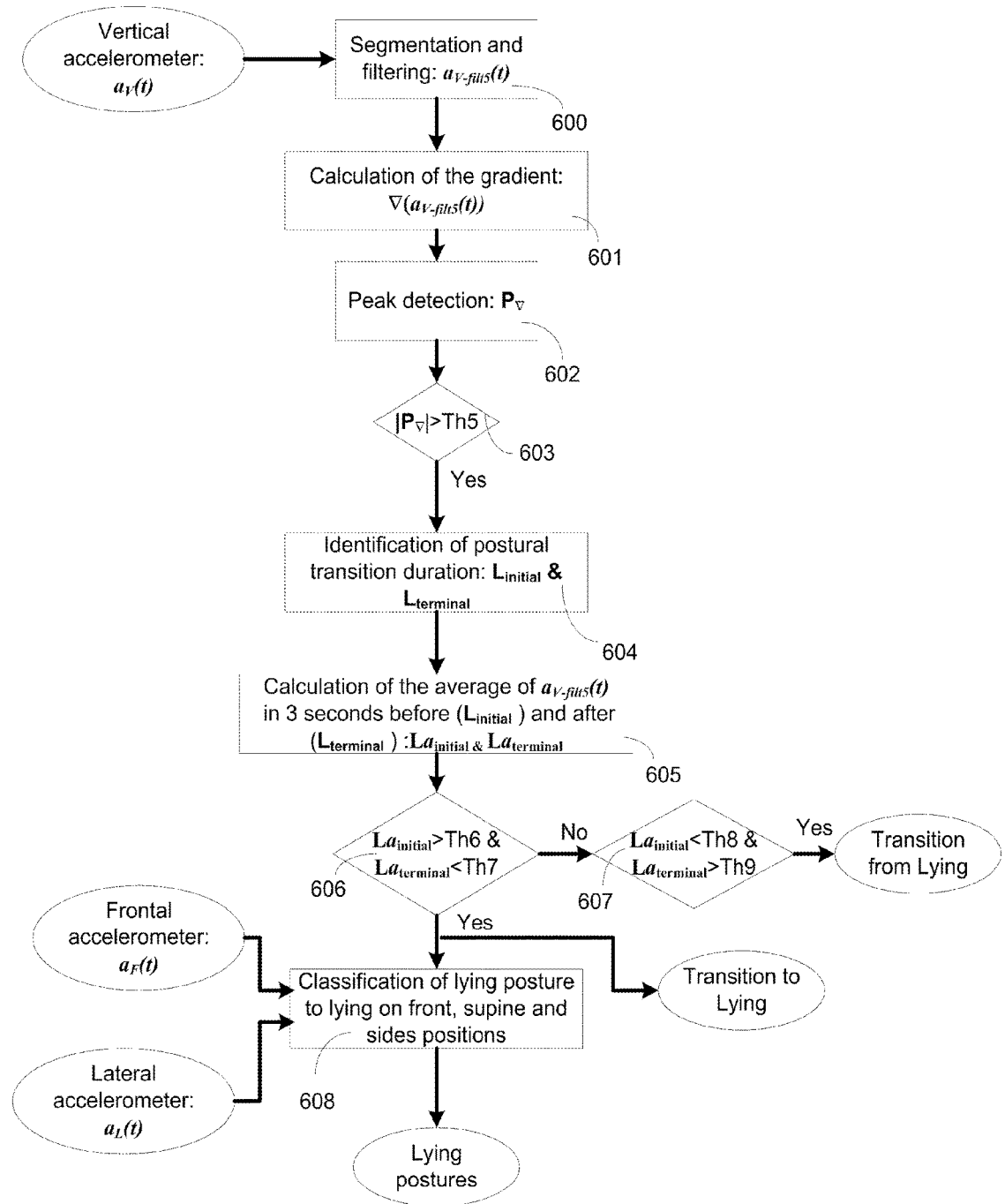
FIG. 6 is a flowchart of the algorithms used to detect and classify the lying posture.

The system identifies both the sit/stand-to-lying (SI/ST-L) and the mirror opposite (i.e., L-SI/ST) postural transitions using the following algorithm:

1) band-pass filter the vertical accelerometer signal (box 600 in FIG. 6);
2) calculate the gradient of the resulting the filtered signal $a_{V\text{-}filt5}(t)$ (box 601 in FIG. 6);
3) determine the maximum or minimum peak ($P_V$) of this gradient (box FIG. 6, box 602);
4) if the absolute value of the detected peak Pv exceeds a pre-defined threshold $Th_5$ (box 603, FIG. 6), estimate the duration of lying postural transition using a local peak detection scheme to identify peaks preceding ($L_{initial}$) and following ($L_{terminal}$) $P_V$ (box 604, FIG. 6);
5) identify a lying posture at the time of the detected peak when (i) the absolute value of the detected peak exceeds a threshold $Th_5$ (box 603, FIG. 6); and (ii) the average value of $a_{V\text{-}filt5}(t)$ during the 3 seconds preceding the $L_{initial}$ is higher than a pre-defined threshold $Th_6$ (boxes 605-606, FIG. 6); and (iii) the average value of $a_{V\text{-}filt5}(t)$ during the 3 seconds following the $L_{terminal}$ is lower than a threshold $Th_7$ (boxes 605-606, FIG. 6);
6) detect/identify a lying-to-sit/stand (L-SI/ST) postural transition at the time of the detected peak $P_V$ when (i) the absolute value of the detected peak exceeds a predefined threshold $Th_5$ (box 603, FIG. 6); and (ii) the average value of $a_{V\text{-}filt5}(t)$ during the 3 seconds preceding the $L_{initial}$ is lower than $Th_8$ (boxes 605-607, FIG. 6); and (iii) the average value of $a_{V\text{-}filt5}(t)$ during the 3 seconds following the $L_{terminal}$ is higher than a threshold $Th_9$ (boxes 605-607, FIG. 6);
7) classify the lying posture further as lying on back, lying on the front, or on the sides (left or right) on the basis of the value of the frontal accelerometer signal (box 608, FIG. 6);
8) further classify lying on the side into lying on the right and lying on the left according to the value of the lateral accelerometer signal.

Figure 7:
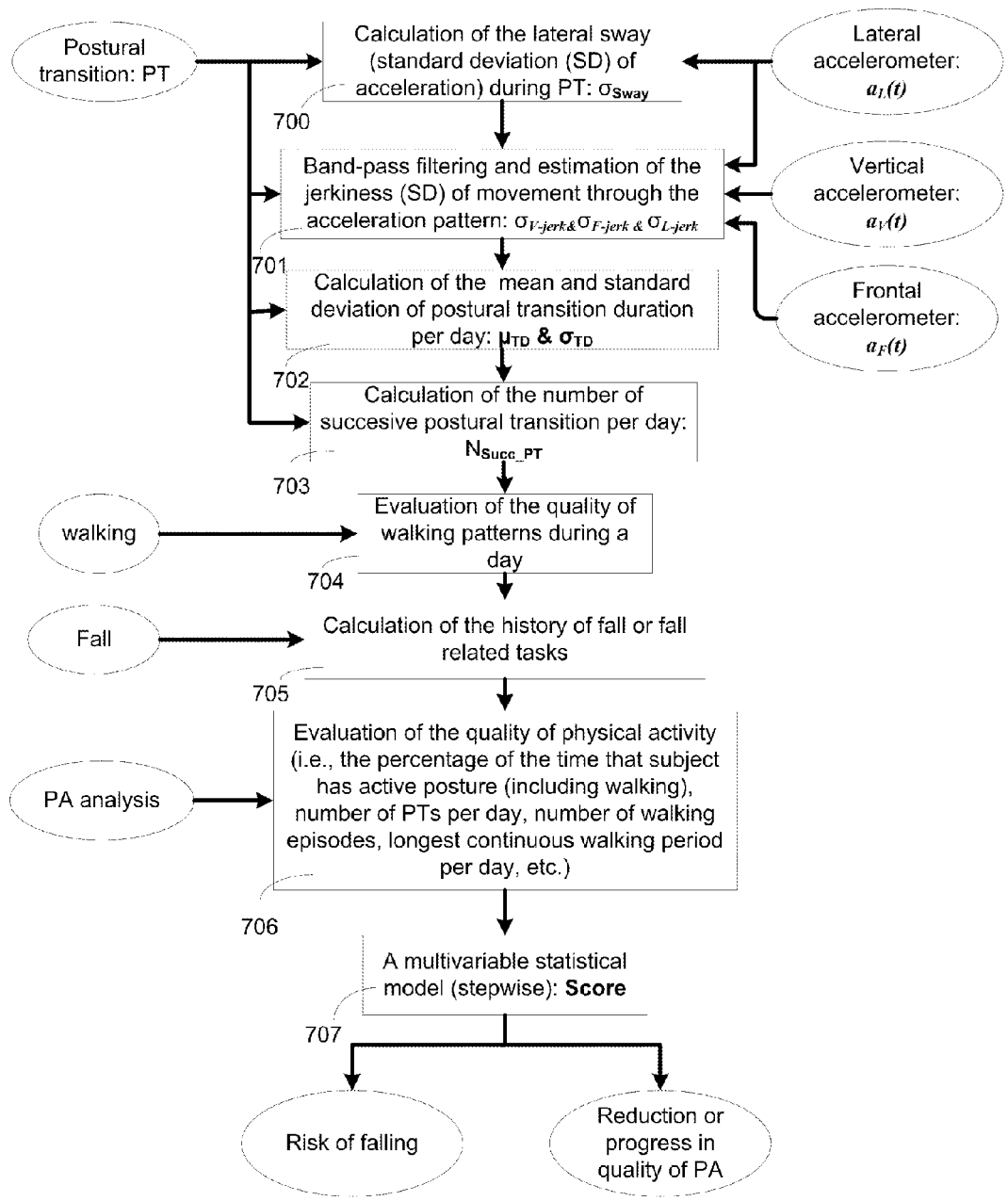
FIG. 7 is a flowchart of the algorithm used to compute the subject's risk of falling, and the quality of the subject's physical activity.

B. Computing the Risk of Falling and the Quality of the Subject's Physical Activity By monitoring the subject's physical activity, the invented system both evaluates the quality of the subject's physical activity, and computes the decline or progress in the subject's functional performance. FIG. 7 presents the flowchart of the corresponding software-based algorithm, developed as part of the invented system.

The subject's risk of falling (RoF) during everyday life is computed by first quantifying the quality of the subject's postural transitions. In turn, the quality of the postural transitions is quantified using the following algorithm:

1) estimate the lateral sway ($\sigma_{sway}$) of the subject during PT by computing the standard deviation of the lateral accelerometer during PT (box 700, FIG. 7);
2) estimate the jerkiness in the subject's movement in all directions ($\sigma_{V\text{-}jerk}$, $\sigma_{F\text{-}jerk}$, and $\sigma_{L\text{-}jerk}$)—computed as the standard deviation of the band-pass filtered acceleration signals in the frontal, vertical and lateral directions (box 701, FIG. 7);
3) compute the mean ($\mu_{TD}$) and standard deviation ($\sigma_{TD}$) of the durations of the subject's postural transitions ($\Delta T_2$), over a day (box 702, FIG. 7);
4) compute the number of successive postural transitions ($N_{Succ\_PT}$) required for a subject to accomplish a single task—an example is multiple unsuccessful attempts by a subject to rise from a chair (box 703, FIG. 7);
5) evaluate the quality of physical activity by computing the fraction of the time that subject has active posture (including walking); the number of PTs per day; the number of walking episodes during a day; and the longest continuous walking period per day (boxes 704-706, FIG. 7);
6) evaluate the subject's risk of falling by inputting the above parameters to a statistical model (e.g., stepwise) that provides a linear combination of the calculated parameters to yield a single score representative the subject's RoF (box 707, FIG. 7). A subject is considered to be at a high-risk of falling if the linear combination passes beyond a threshold, which may be pre-defined, or may change adaptively.

To identify a subject at a high risk of falling more accurately, the system continually adjusts the requisite threshold values based on the history of falls or other similar events detected by the algorithm (e.g., high-impact experienced shortly after a postural transition, very short ST-SI durations, etc.)

I. Automatic Fall Detection.

Figure 8:
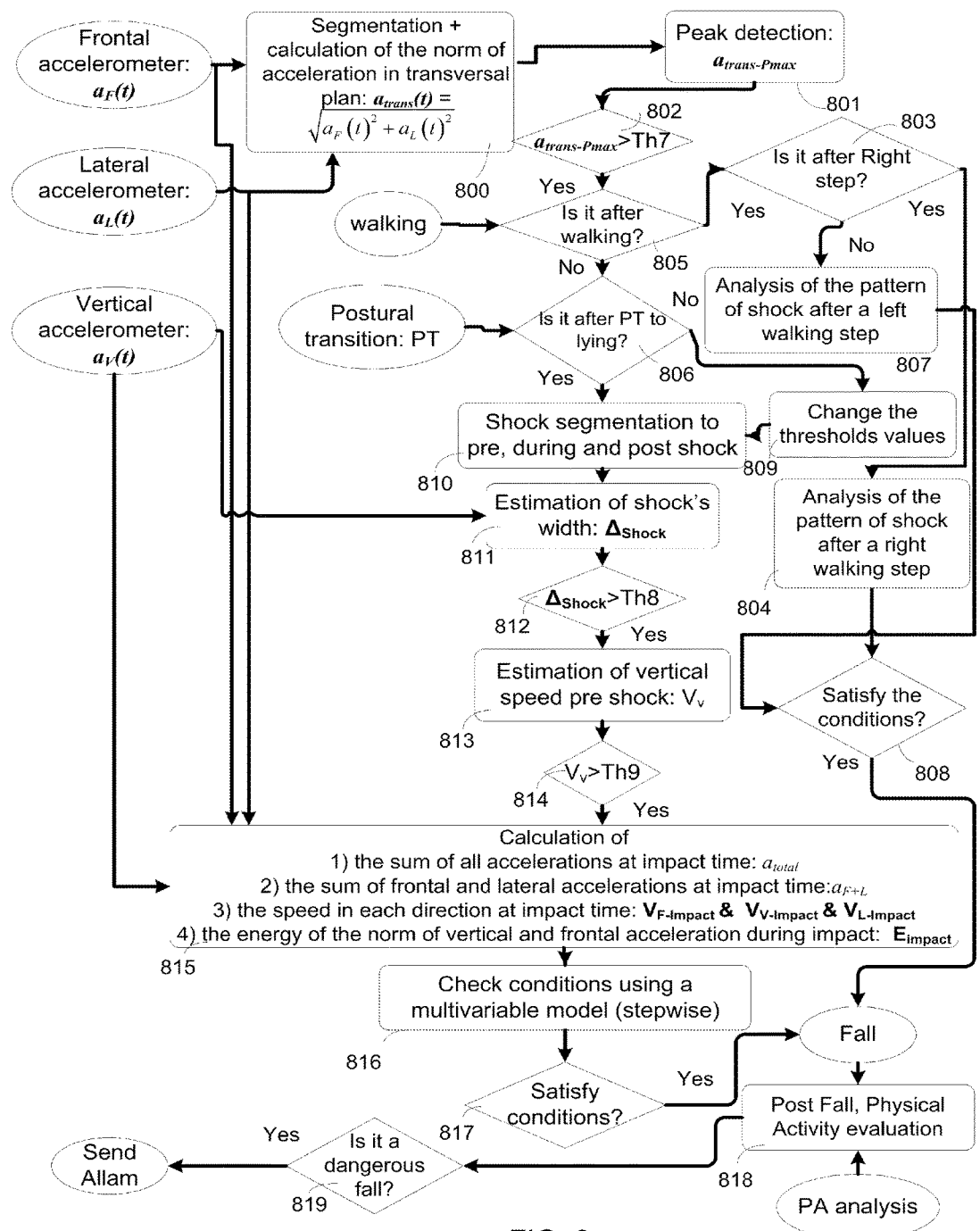
FIG. 8 is a flowchart of the algorithm used to automatically detect the subject's falls.

The present invention uses a novel algorithm, based solely on accelerometer signals, to automatically identify falls during the subject's everyday life with high sensitivity and specificity. The fall-detection algorithm described here uses information about the subject's physical activity, as well as posture. The flowchart in FIG. 8 describes in complete the algorithm developed to automatically detect the subject's falls. The following summarizes the algorithm:

1) compute the norm (magnitude) of acceleration in the transversal plane, $a_{trans}(t)$ from the frontal and lateral acceleration signals—$a_F(t)$ and $a_L(t)$, respectively—through:

$$a_{trans}(t)=\sqrt{[a_F(t)]^2+[a_v(t)]^2}_{(box\ 800)};$$

2) apply a peak-detection algorithm (box 801) to atrans(t) to identify the presence of "shocks" $a_{trans-Pmax}$;
3) confirm a fall event by considering the subject's PA and posture prior to impact times (marked by the identified shocks)—this step is carried out using algorithms described above;
4) use different algorithms to identify a fall event, depending on the results of step (3) supra:
   if impacts occur while subject is walking or turning, depending on whether the impacts occurred after right or left step, the algorithm chooses appropriate thresholds and coefficients required for subsequent steps ($Th_8$: box 812; $Th_9$: box 814; and coefficients of the multivariable model: box 816);
   (ii) if activity preceding the shock is not identified as walking, turning or any sequential locomotion (e.g., walking upstairs or downstairs,) the algorithm would identify as fall events only the shocks that occur after a postural transition to sitting or lying.
   (iii) Next, thresholds and coefficients required for subsequent steps are modified;
5) segment the shock-pattern following a postural transition into pre-shock, impact, and post-shock phases based on the location of local minimum peaks relative to the absolute maximum peak ($p_{max}$) in the signal $a_{trans}(t)$ (box 810, FIG. 8); the set of thresholds chosen according to step (4) supra, and used by the algorithm depends on whether the post-shock posture is sitting or lying.
6) estimate the shock width ($\Delta_{shock}$) using the local minimum peaks before and after each the peak $p_{max}$ (box 811, FIG. 8); consider the peak to be an artifact and subsequently ignored if its width does not exceed the threshold $Th_8$ (box 812, FIG. 8);
7) if the peak is not an artifact, compute the subject's speed during the pre-shock phase by integrating the pattern of vertical accelerometer—$V_V(t)$ (box 813, FIG. 8); for the peak to be recognized as a fall, the peak of the velocity profile must exceed the threshold $Th_9$ (box 814, FIG. 8);
8) compute the following descriptors (box 815, FIG. 8):
   (i) sum of all accelerations at the time of impact $t_{impact}$ as:

$$a_{total}(t_{impact})=a_F(t_{impact})+a_V(t_{impact})+a_V(t_{impact});$$

(ii) the sum frontal and lateral accelerations at impact time:

$$a_{F+L}(t_{impact})=a_F(t_{impact})+a_L(t_{impact});$$

(iii) the difference of speed in each direction at the impact time ($V_{F-impact}$, $V_{V-impact}$, and $V_{L-impact}$); and
   (iv) energy of the norm of vertical and frontal acceleration during the impact phase ($\Delta_{shock}$):

$$E_{Impact} = \int_{\Delta Shock} \sqrt{a_F(t)^2 + a_V(t)^2}\, dt\,;$$

9) identify a fall event through a multivariable model (stepwise or linear combination) that uses the above descriptors as inputs and coefficients chosen in step (4) supra (box 816, FIG. 8);
10) identify a fall as "serious" if the post-fall activities represent an unusual activity pattern, such as a long-duration rest, or multiple unsuccessful postural transitions (boxes 818-819, FIG. 8); in one embodiment of the invention, an alarm will be set off following a "serious" fall;

II. Physical Activity Classification.

The algorithms described above will classify the subject's physical activity and posture, determine his or her risk of falling and quality of movements. In addition, several rules will be applied to improve the classifications performed by the above algorithms. These rules include, but are not limited to, the following:
1) If two contradictory states are detected (e.g., lying with walking or sitting with walking) preference is first given to lying, then to walking, and finally to postural transitions. This rule is based on the rationale that the lying posture is classified with the least amount of error. It should be noted that since the algorithms for different postural detections operate independently, two contradictory sets of activities may be identified.
2) Two successive postural transitions classified as the same type (e.g., SI-ST followed by SI-ST) are not possible—the classifications are modified according to the preceding and subsequent activities.
3) Elderly subjects cannot lean backwards after a SI-ST transition with a high likelihood. The algorithm estimates the trunk lean angle based on the trunk angle before ($\theta_{PT-pre}$) and/or following ($\theta_{PT-post}$) the postural transition.
   (i) Both $\theta_{PT-pre}$ and $\theta_{PT-post}$ are estimated based on the mean (E[.]) of the frontal acceleration during the rest period immediately before, or after a postural transition, according to the following formulas:

$$\theta_{PT-pre}=\sin^{-1}(E[a_F(t)|\text{pre-PT-rest}])$$

$$\theta_{PT-post}=\sin^{-1}(E[a_F(t)|\text{post-PT-rest}])$$

where $E[a_F(t)$ pre-PT-rest] denotes the mean of the frontal acceleration signal during the rest period immediately before the postural transition; $E[aF(t)|\text{post-PT-rest}]$ denotes the corresponding mean after the postural transition.
   (ii) If the standard deviation of both frontal and vertical accelerations during a local interval before or after a postural transition were lower than a pre-defined threshold, the algorithm will classify that duration as a rest period.
   (iii) Sensor inclination ($\theta_{initial}$) is computed from the average of the frontal accelerometer signal during a recognized walking episode containing at least 10 steps: $\theta_{initial}=\sin^{-1}(E[a_F(t)|\text{walking; 10 steps}])$.
   (iv) The backwards-leaning state is detected if, subtracting $\sigma_{initial}$ from $\theta_{PT-pre}$ (or $\theta_{PT-post}$) yields a value lower than a pre-defined threshold.
4) The duration of the lying posture should be more than a specified length (e.g., 30 seconds).
5) For an episode to be classified as "walking," it must include at least three successive steps within a pre-defined interval.
6) Since it is improbable for a person, especially an elderly subject, to stand for long periods without any movements, long standing periods without additional activity (e.g., more than three minutes) are interpreted as sitting. This rule applies if the standard deviations of both the vertical and frontal accelerations are below pre-defined thresholds.

REFERENCES

[1] B. Najafi and K. Aminian, "Body movement monitoring system for elderly people, determines time and duration of postural transition (2000, European and US patent)," EP1195139-A1 EP810920 5 Oct. 2000; US2004015103-A1 US398462 4 Apr. 2003, 2000.
[2] B. Najafi, K. Aminian, F. Loew, Y. Blanc, and P. A. Robert, "Measurement of stand-sit and sit-stand transitions using a miniature gyroscope and its application in fall risk evaluation in the elderly," *Ieee Transactions on Biomedical Engineering*, vol. 49, pp. 843-851, 2002.
[3] B. Najafi, K. Aminian, A. Paraschiv-Ionescu, F. Loew, C. J. Bula, and P. Robert, "Ambulatory system for human motion analysis using a kinematic sensor: Monitoring of daily physical activity in the elderly," *Ieee Transactions on Biomedical Engineering*, vol. 50, pp. 711-723, 2003.
[4] R. W. Bohannon, A. W. Andrews, and M. W. Thomas, "Walking speed: reference values and correlates for older adults," *J Orthop Sports Phys Ther*, vol. 24, pp. 86-90, 1996.
[5] K. Aminian, B. Najafi, C. Bula, P. F. Leyvraz, and P. Robert, "Spatio-temporal parameters of gait measured by an ambulatory system using miniature gyroscopes," *Journal of Biomechanics*, vol. 35, pp. 689-699, 2002.
[6] K. Aminian, B. Najafi, J. Gramiger, P. Morel, and N. Bijan, "Autonomous measuring unit for human movement has sensors, conditioning circuit, display, and circuit for recording kinematic parameters of body segment," ECOLE POLYTECHNIQUE FEDERALE LAUSANNE (ECOL-Non-standard) AMINIAN K (AMIN-Individual) BIJAN N (BIJA-Individual) GRAMIGER J (GRAM-Individual) MOREL P (MORE-Individual).
[7] K. Aminian, K. Rezakhanlou, E. De Andres, C. Fritsch, P. F. Leyvraz, and P. Robert, "Temporal feature estimation during walking using miniature accelerometers: an analysis of gait improvement after hip arthroplasty," *Medical & Biological Engineering & Computing*, vol. 37, pp. 686-691, 1999.
[8] S. R. Cummings, M. C. Nevitt, and S. Kidd, "Forgetting falls. The limited accuracy of recall of falls in the elderly," *J Am Geriatr Soc*, vol. 36, pp. 613-6, 1988.
[9] D. Oliver, M. Britton, P. Seed, F. C. Martin, and A. H. Hopper, "Development and evaluation of evidence based risk assessment tool (STRATIFY) to predict which elderly inpatients will fall: case-control and cohort studies," *Bmj*, vol. 315, pp. 104953, 1997.
[10] M. E. Tinetti, T. F. Williams, and R. Mayewski, "Fall risk index for elderly patients based on number of chronic disabilities," *Am J Med*, vol. 80, pp. 429-34, 1986.
[11] K. Doughty, R. Lewis, and A. McIntosh, "The design of a practical and reliable fall detector for community and institutional telecare," *J Telemed Telecare*, vol. 6 Suppl 1, pp. S150-4, 2000.
[12] U. Lindemann, A. Hock, M. Stuber, W. Keck, and C. Becker, "Evaluation of a fall detector based on accelerometers: a pilot study," *Med Biol Eng Comput*, vol. 43, pp. 548-51, 2005.
[13] Y. Depeursinge, J. Krauss, and M. El-Khoury, "Device for monitoring the activity of a person and/or detecting a fall, U.S. Pat. No. 6,201,476," 2001.
[14] N. Noury, G. Barralon, G. Virone, P. Boissy, M. Hamel, and P. Rumeau, "A smart sensor based on rules and its evaluation in daily routines," presented at 25th Annual International Conference of the IEEE Eng. Med. Biol. Society, 2003.

What is claimed is:

1. A body movement monitoring system comprising:
a data processing system comprising one or more processor circuits configured to process data generated by a sensor, the data including information representative of at least one signal generated by the sensor in response to movement of an upper part of a body of a person, the data processing system programmed to at least:
process said data to identify one or more peaks in the at least one signal by comparing one or more parameters with one or more predefined fall thresholds; and
for at least one identified peak of the one or more peaks:
process said data to identify a non-fall activity performed by the person during at least one of a time period before said identified peak or a time period after said identified peak; and
in response to identifying said non-fall activity:
determine whether said identified peak can be classified as a fall event or a non-fall event based on the one or more predefined fall thresholds;
in response to determining said identified peak can be classified as a fall event or a non-fall event based on the one or more predefined fall thresholds, classify said identified peak as a fall event or a non-fall event based on the one or more predefined fall thresholds; and
in response to determining said identified peak cannot be classified as a fall event or a non-fall event based on the one or more predefined fall thresholds:
set one or more new fall thresholds based on said non-fall activity;
process a portion of the data corresponding to a time window that encompasses said identified peak to compute one or more parameters; and
determine whether to classify said identified peak as a fall event by comparing said one or more parameters to said one or more new fall thresholds.

2. The system of claim 1 wherein said non-fall activity is walking, sitting, standing, or lying down.

3. The system of claim 1 wherein said one or more new fall thresholds are set based on at least one of the following:
body posture during the time period prior to the time window corresponding to the identified peak; or
body posture during the time period following the time window corresponding to the identified peak.

4. The system of claim 1 wherein:
the sensor comprises at least one accelerometer; and
at least one of said one or more processor circuits is programmed to determine at least one posture of the person based on a direction of an acceleration measured by the at least one accelerometer, the acceleration being relative to a gravitational acceleration.

5. The system of claim 1 wherein said one or more parameters include or are calculated based on at least one of:
a speed at a time prior to said identified peak or during a time period that encompasses said identified peak;

an acceleration during a time period that encompasses said identified peak; or a mechanical energy during a time period that encompasses said identified peak.

6. The system of 5 wherein said one or more processor circuits are further programmed to set said one or more new fall thresholds based at least in part on information derived from the person's movement over a period of time prior to said identified peak.

7. The system of 6 wherein said information derived from the person's movement includes at least one of:

a measure of walking; or a measure of postural transitions.

8. The system of claim 1 further comprising a communications system configured to receive said data from said sensor.

9. The system of claim 1 further comprising the sensor.

10. The system of claim 9 wherein the sensor is attached to the upper part of the body.

11. The system of claim 9 wherein the sensor comprises at least one of the one or more processor circuits configured to process said data generated by said sensor.

12. The system of claim 11 wherein the at least one of the one or more processor circuits of the sensor is configured to at least partially process said data generated by said sensor.

13. The system of claim 9 wherein the sensor entirely houses the one or more processor circuits configured to process said data generated by said sensor.

14. The system of claim 1 wherein the data processing system comprising said one or more processor circuits configured to process said data generated by said sensor is housed separately from said sensor.

15. The system of claim 1 wherein said information derived from the person's movement includes a history of fall events.

16. The system of claim 1 further comprising one or more data storage systems configured to store at least one of the data generated by said sensor or data processed by said one or more processor circuits.

17. The system of claim 1 wherein setting the one or more new fall threshold is based on a type of non-fall activity identified.

18. The system of claim 17 wherein said type of non-fall activity comprises walking, sitting, standing, or lying down.

19. The system of claim 18 wherein said type of non-fall activity comprises walking and said one or more new fall thresholds is based on either walking on a right step or walking on a left step.

20. The system of claim 1 wherein said one or more processor circuits are further configured to:

determine information related to physical activity of the person after a time period corresponding to the identified peak in response to classifying said identified peak as a fall event; and classify the fall event as a serious fall event when the determined information indicates that the fall event is followed by a long period of rest or multiple unsuccessful postural transitions in succession.

21. The system of claim 1 wherein said one or more processor circuits are further configured to:

when the identified non-fall activity is not walking, segment a shock pattern identified based on the one or more peaks;

estimate a width of the shock pattern; and estimate a vertical speed of the person in a time period prior to a time period corresponding to the shock pattern.

22. A body movement monitoring system comprising:

a data processing system comprising one or more processor circuits configured to process data generated by a sensor, the data including information representative of at least one signal generated by the sensor in response to movement of an upper part of a body of a person, the data processing system programmed to at least:

process said data to identify one or more peaks in the at least one signal by comparing one or more parameters with one or more predefined fall thresholds; and for at least one identified peak of the one or more peaks:

process said data to identify a non-fall activity performed by the person during at least one of a time period before said identified peak or a time period after said identified peak; and in response to identifying said non-fall activity:

set one or more new fall thresholds based on said non-fall activity;

process a portion of the data corresponding to a time window that encompasses said identified peak to compute one or more parameters; and determine whether to classify said identified peak as a fall event by comparing said one or more parameters to said one or more new fall thresholds.

23. The system of claim 22 further comprising the sensor, wherein the sensor is attached to the upper part of the body.

24. The system of claim 22 wherein said non-fall activity is walking, sitting, standing, or lying down.

25. The system of claim 22 wherein said one or more new fall thresholds are set based on at least one of the following:

body posture during the time period prior to the time window corresponding to the identified peak; or body posture during the time period following the time window corresponding to the identified peak.

26. The system of claim 22 further comprising the sensor, wherein:

the sensor comprises at least one accelerometer; and at least one of said one or more processor circuits is programmed to determine at least one posture of the person based on a direction of an acceleration measured by the at least one accelerometer, the acceleration being relative to a gravitational acceleration.

27. The system of claim 22 further comprising a communications system configured to receive said data from said sensor.

28. The system of claim 22 wherein the data processing system comprising said one or more processor circuits configured to process said data generated by said sensor is housed separately from said sensor.

29. The system of claim 22 wherein said information derived from the person's movement includes a history of fall events.

30. The system of claim 22 wherein said one or more processor circuits are further configured to:

determine information related to physical activity of the person after a time period corresponding to the identified peak in response to classifying said identified peak as a fall event; and classify the fall event as a serious fall event when the determined information indicates that the fall event is followed by a long period of rest or multiple unsuccessful postural transitions in succession.

31. The system of claim 22 wherein said one or more processor circuits are further configured to:

when the identified non-fall activity is not walking, segment a shock pattern identified based on the one or more peaks;
estimate a width of the shock pattern; and
estimate a vertical speed of the person in a time period prior to a time period corresponding to the shock pattern.

\* \* \* \* \*

UNITED STATES PATENT AND TRADEMARK OFFICE
CERTIFICATE OF CORRECTION

PATENT NO. : 9,901,290 B2  
APPLICATION NO. : 14/659446  
DATED : February 27, 2018  
INVENTOR(S) : Bijan Najafi et al.

Page 1 of 2

It is certified that error appears in the above-identified patent and that said Letters Patent is hereby corrected as shown below:

In the Drawings

Drawing Sheet 2 of 10 (Reference Numeral 210) (FIG. 2) Line 1, Change "sagital" to --sagittal--.

Drawing Sheet 9 of 10 (Reference Numeral 703) (FIG. 7) Line 2, Change "succesive" to --successive--.

Drawing Sheet 10 of 10 (Reference Numeral 801) (FIG. 8) Line 2, Change "$a_{trans-Pmax}$" to --$a_{trans}\text{-}P_{max}$--.

Drawing Sheet 10 of 10 (Reference Numeral 802) (FIG. 8) Line 1, Change "$a_{trans-Pmax}$" to --$a_{trans}\text{-}P_{max}$--.

Drawing Sheet 10 of 10 (FIG. 8) at Line 39 (Approx.), Change "Allam" to --Alarm--.

In the Specification

Column 6 Line 51, Change "Th1;" to --$Th_1$;--.

Column 6 Line 54, Change "306 see" to --306—see--.

Column 7 Line 4, Change "ΔT1" to --$\Delta T_1$--.

Column 7 Line 10, Change "aF(t)" to --$a_F(t)$--.

Column 8 Line 50, Change "aV-filt3(t)" to --$a_{V\text{-}filt3}(t)$--.

Column 9 Line 44, Change "(Pv)" to --$(P_\nabla)$--.

Signed and Sealed this  
Twenty-eighth Day of August, 2018

Andrei Iancu  
*Director of the United States Patent and Trademark Office*

CERTIFICATE OF CORRECTION (continued)
U.S. Pat. No. 9,901,290 B2

Column 9 Line 46, Change "Pv" to --$P_V$--.

Column 9 Line 60, Change "Pv" to --$P_V$--.

Column 11 Line 8, Change "atrans(t)" to --$a_{trans}(t)$--.

Column 11 Line 9, Change "$a_{trans-Pmax}$;" to --$a_{trans}$-$P_{max}$;--.

Column 11 Line 16, Before "if" insert --(i)--.

Column 11 Line 26, Change "lying." to --lying;--.

Column 11 Line 36, Change "lying." to --lying;--.

Column 12 Line 43, Change "E[$a_F$(t) pre–PT–rest]" to --E[$a_F$(t)|pre–PT–rest]--.

Column 12 Line 55, Change "10" to --ten--.

Column 12 Line 58, Change "$\sigma_{initial}$" to --$\theta_{initial}$--.

Column 12 Line 58, Change "$\theta_{PT-pre}$(or $\theta_{PT-post}$)" to --$\theta_{PT-pre}$ (or $\theta_{PT-post}$)--.

In the Claims

Column 15 Line 5, Claim 6, after "system of" insert --claim--.

Column 15 Line 10, Claim 7, after "system of" insert --claim--.